(12) United States Patent
Suehara

(10) Patent No.: US 9,113,783 B2
(45) Date of Patent: Aug. 25, 2015

(54) FLEXIBLE TUBE FOR MEDICAL INSTRUMENT AND MEDICAL INSTRUMENT

(71) Applicant: TERUMO KABUSHIKI KAISHA, Shibuya-ku (JP)

(72) Inventor: Satoru Suehara, Ashigarakami-gun (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 13/779,064

(22) Filed: Feb. 27, 2013

(65) Prior Publication Data
US 2013/0226151 A1 Aug. 29, 2013

(30) Foreign Application Priority Data
Feb. 28, 2012 (JP) ................................ 2012-042248

(51) Int. Cl.
*A61B 1/00* (2006.01)
*A61M 25/00* (2006.01)
(Continued)

(52) U.S. Cl.
CPC ............... *A61B 1/0055* (2013.01); *A61B 1/008* (2013.01); *A61M 25/0138* (2013.01); *A61M 39/1055* (2013.01); *A61M 25/0051* (2013.01)

(58) Field of Classification Search
CPC .. A61B 1/0055; A61B 1/0051; A61B 1/0008; A61B 2017/00314; A61B 1/0056; A61B 1/00105; A61M 25/0138; A61M 25/0067; A61M 25/0068
USPC ................... 604/523, 535; 600/139, 141, 142
See application file for complete search history.

(56) References Cited

U.S. PATENT DOCUMENTS 5,807,241 A * 9/1998 Heimberger ................... 600/142
6,364,828 B1 * 4/2002 Yeung et al. ................... 600/142
(Continued)

FOREIGN PATENT DOCUMENTS

DE 10 2005 054 057 A1 6/2007
EP 0 782 836 A1 7/1997
(Continued)

OTHER PUBLICATIONS

Notification of Transmittal of the International Search Report (Forms PCT/ISA/220 and PCT/ISA/210) and the Written Opinion of the International Searching Authority (Form PCT/ISA/237) issued on Jul. 11, 2013, in the corresponding International Application No. PCT/JP2013/001011. (14 pages).

*Primary Examiner* — Nicholas Lucchesi
*Assistant Examiner* — Leah Stohr
(74) *Attorney, Agent, or Firm* — Buchanan, Ingersoll & Rooney PC

(57) ABSTRACT

A flexible tube for medical instrument includes tubular bodies, one of the tubular bodies relatively turnably connected to an adjacent one of the tubular bodies by a hinge structure. Each of the tubular bodies includes a pivotal section provided at a connecting-directionally first end edge forming the hinge structure, a turning support section provided at a connecting-directionally second end edge and supporting the pivotal section of the one of tubular bodies connected to the adjacent one of tubular bodies, a projection which is provided at either one of the first and second end edges, and is projected in the connecting direction from a position different from the position of the pivotal section or the turning support section, and a recess provided at the other of the first and second end edges and engaged with the projection of the one of tubular bodies connected to the adjacent one of tubular bodies.

7 Claims, 12 Drawing Sheets

(51) Int. Cl.
  *A61B 1/005* (2006.01)
  *A61M 39/10* (2006.01)
  *A61B 1/008* (2006.01)
  *A61M 25/01* (2006.01)

(56) References Cited

U.S. PATENT DOCUMENTS 7,578,786 B2 *   8/2009   Boulais et al. ................ 600/142

2004/0254450 A1   12/2004   Griffin et al.
2008/0249364 A1   10/2008   Korner

FOREIGN PATENT DOCUMENTS

| EP | 1 977 677 A1 | 10/2008 |
| EP | 2 581 031 A1 | 4/2013 |
| JP | 2007-500068 A | 1/2007 |

* cited by examiner

FLEXIBLE TUBE FOR MEDICAL INSTRUMENT AND MEDICAL INSTRUMENT

CROSS-REFERENCE TO RELATED APPLICATION

The present disclosure contains subject matter related to that disclosed in Japanese Priority Patent Application JP 2012-042248 filed in the Japan Patent Office on Feb. 28, 2012, the entire content of which is hereby incorporated by reference.

BACKGROUND OF THE INVENTION

The present invention relates to a flexible tube for medical instrument and to a medical instrument.

As a medical instrument (device) such as catheter or endoscope, there has been known one in which a flexible tube is used as an introduction section for introduction into a living body so that the introduction section can be curved (see, for example, JP-A-2007-500068, hereinafter referred to as Patent Document 1).

The flexible tube described in Patent Document 1 includes a plurality of tubular members connected together so that they can be turned (rotated) relative to one another. The flexible tube can be curved as the tubular members are turned relative to one another.

SUMMARY OF THE INVENTION

Meanwhile, when a flexible tube for medical instrument is introduced into a living body, external forces such as torsional forces, tensile forces and bending forces are exerted on the flexible tube. Therefore, rigidity of the flexible tube against such external forces has to be secured.

However, the flexible tube described in Patent Document 1 cannot show sufficient rigidity, since it is configured to receive external forces by only pivotal parts, such as hinges. To cope with this problem, it may be contemplated to add a reinforcement member to the flexible tube, thereby securing the required rigidity. This approach, however, is disadvantageous because it adversely affects the flexible tube, by increasing the outside diameter or reducing the lumen of the flexible tube.

In addition, in the flexible tube described in Patent Document 1, the end edges of the adjacent tubular members are spaced from each other. This leads to a problem that when an inserted body such as a guide wire is inserted into and passed through the lumen of the flexible tube, the inserted body would be caught on the end edge of the tubular member, so that it takes much time to insert and pass the inserted body through the lumen.

It is an object of the present invention to provide a flexible tube for medical instrument which can securely have sufficient rigidity and which permits an inserted body to be inserted thereinto and passed therethrough easily, and to provide a medical instrument having such a flexible tube.

According an aspect of the present invention, there is provided a flexible tube for medical instrument, including a plurality of tubular bodies, one of the plurality of tubular bodies relatively turnably connected to an adjacent one of the plurality of tubular bodies by a hinge structure, in which each of the tubular bodies includes a pivotal section which is provided at a connecting-directionally first end edge and forms the hinge structure, a turning support section which is provided at a connecting-directionally second end edge and supports the pivotal section of the one of the plurality of tubular bodies connected to the adjacent one of the plurality of tubular bodies, a projection which is provided at either one of the first end edge and the second end edge, and which is projected in the connecting direction from a position different from the position of the pivotal section or the turning support section, and a recess which is provided at the other of the first end edge and the second end edge, and which is engaged with the projection of the one of the plurality of tubular bodies connected to the adjacent one of the plurality of tubular bodies.

According to the present invention, the recess of each tubular body is engaged with the projection of the tubular body connected to the tubular body under consideration. Therefore, external forces exerted on the flexible tube for medical instrument can be received by the recesses and the projections. Thus, external forces can be received also by other sections than the pivotal sections and turning support sections. Consequently, sufficient rigidity against external forces can be secured.

In addition, since the projection of each tubular body is engaged with the recess of the tubular body connected to the tubular body under consideration, the tubular bodies are bridged to one another by the projections. This permits a body inserted into the flexible tube to be guided while making contact with the projections. Therefore, the inserted body would not easily be caught on the connecting-directionally end edges of the tubular bodies, so that the inserted body can be easily inserted into and passed through the flexible tube.

In the flexible tube for medical instrument according to the above aspect of the invention, preferably, the recess has a sliding contact part which is so formed that its width in a direction orthogonal to a depth direction of the recess is constant along the depth direction and with which the projection makes sliding contact.

According to this configuration, the recess is provided with the sliding contact part which extends along the depth direction and with which the projection makes sliding contact. This ensures that the recess and the projection continue to make contact with each other in their width direction, namely, in the circumferential direction of the tubular bodies, irrespectively of the curved degree of the flexible tube. Therefore, when a rotating force about the axis of the tubular bodies is exerted on the flexible tube, the rotating force can be received also by other sections than the pivotal sections. Accordingly, it is possible to enhance torsional rigidity of the flexible tube and to further enhance rigidity of the flexible tube.

In the flexible tube for medical instrument according to the above aspect of the invention, preferably, a tip edge of the projection makes contact with a bottom edge of the recess.

According to this configuration, the tip edge of the projection makes contact with the bottom edge of the recess. This ensures that when a compressive force is exerted on the flexible tube, the compressive force can be received also by other sections than the pivotal sections. This promises a flexible tube with an enhanced compressive rigidity and a more enhanced rigidity.

In the flexible tube for medical instrument according to the above aspect of the invention, preferably, a configuration is adopted in which the projection and the recess are provided on either of one side and the other side of a turning axis of the hinge structure, the tip edge of the projection on the one side makes contact with the bottom edge of the recess on the one side when the flexible tube is in a straight state, and the tip edge of the projection on the other side makes contact with the bottom edge of the recess on the other side when the flexible tube is bent.

In this configuration, the contact between the tip edge of the projection and the bottom edge of the recess is secured both in the straight state and in the curved state of the flexible tube. Therefore, a compressive force can be received also by other sections than the pivotal sections, both in the case where the flexible tube is in a straight state and in the case where the flexible tube is in a curved state. Consequently, compressive rigidity of the flexible tube can be further enhanced.

In the flexible tube for medical instrument according to the above aspect of the invention, preferably, a configuration is adopted in which the projection has an enlarged-width part whose width in a direction orthogonal to a projecting direction of the projection gradually increases along the projecting direction, and the recess has a reduced-width part whose width in a direction orthogonal to a depth direction of the recess gradually decreases along the depth direction.

According to this configuration, even when the projection is moved in a direction for disengagement from the recess due to enlargement of the spacing between the recess located at an outer side of the curved portion and the projection engaged therewith in accordance with the curving of the flexible tube, the enlarged-width part of the projection is fitted into the reduced-width part of the recess in a wedge-like manner. Thus, since the projection is caught on the recess, tensile rigidity of the flexible tube in the curving direction can be enhanced, and rigidity of the flexible tube can be more enhanced. Furthermore, when the recess and the projection located on the inner side of curvature are preliminarily engaged with each other, with the enlarged-width part of the projection being fitted in the reduced-width part of the recess in a wedge-like manner, when the flexible tube is in a straight state, tensile rigidity of the flexible tube in the straight state can also be enhanced.

In the flexible tube for medical instrument according to the above aspect of the invention, preferably, the recess has a sliding contact part which is so formed that its width in a direction orthogonal to a depth direction of the recess is constant along the depth direction and with which the projection makes sliding contact, and a maximum-width portion of the enlarged-width part makes sliding contact with the sliding contact part.

According to this configuration, since the maximum-width portion of the enlarged-width part makes sliding contact with the sliding contact part of the recess, it is unnecessary to provide other part for sliding contact with the recess than the enlarged-width part. Therefore, the sliding contact state between the projection and the recess can be maintained while suppressing the amount of projection of the projection and the depth of the recess. This makes it possible to enhance rigidity of the projection and the recess, and to shorten the tubular bodies to be connected together. Accordingly, it is possible to further enhance rigidity of the flexible tube and to shorten the curved portion of the flexible tube.

In the flexible tube for medical instrument according to the above aspect of the invention, preferably, a tip edge of the projection is curved to bulge in a projecting direction of the projection, and a bottom edge of the recess is curved to bulge in a depth direction of the recess.

According to this configuration, since the tip edge of the projection and the bottom edge of the recess are formed in curved line shapes, a body inserted into the flexible tube can be guided along the shape of the tip edge or the bottom edge. This makes it possible to restrain the inserted body from being caught on the tip edge or the bottom edge. Consequently, the inserted body can be speedily inserted into and passed through the flexible tube.

In the flexible tube for medical instrument according to the above aspect of the invention, preferably, connecting-directionally end edges of each tubular body are so formed that the width of the tubular body in the connecting direction gradually decreases as the distance from the turning axis of the hinge structure increases.

According to this configuration, connecting-directionally end edges of each tubular body are so formed that the width of the tubular body in the connecting direction gradually decreases as the distance from the turning axis of the hinge structure increases. This ensures that the spacing between the opposed end edges of the tubular bodies connected to each other increases as the distance from the turning axis increases. Therefore, even in the case where the spacing between the end edges is reduced due to turning of the tubular bodies when the flexible tube is curved, these end edges can be prevented from interfering with each other.

According to another aspect of the present invention, there is provided a medical instrument including: the above-mentioned flexible tube for medical instrument according to the present invention; and position fixing unit that is adapted to fix a curved position of the flexible tube.

According to the present invention as just-mentioned, it is possible to obtain a medical instrument which exhibits the effects of the above-mentioned flexible tube for medical instrument.

The medical instrument according to the above aspect of the invention preferably includes an expansion body which is provided on an outer circumference of the flexible tube or is provided in the flexible tube so as to be capable of being advanced and retracted and which is expanded in a radial direction of the flexible tube.

According to this configuration, the flexible tube for medical instrument can be inserted into a living body in a freely curvable manner, while securing rigidity against external forces. Besides, by expanding the expansion body in a stenosed part in a living body, it is possible to dilate and treat the stenosed part.

DETAILED DESCRIPTION OF THE PREFERRED EMBODIMENTS

Now, some embodiments of the present invention will be described below, based on the drawings.

Incidentally, in second and later embodiments, component members which are the same as or functionally equivalent to those described in the following first embodiment will be denoted by the same reference signs as used in the first embodiment, and descriptions of them will be omitted or simplified.

First Embodiment

Figure 1:
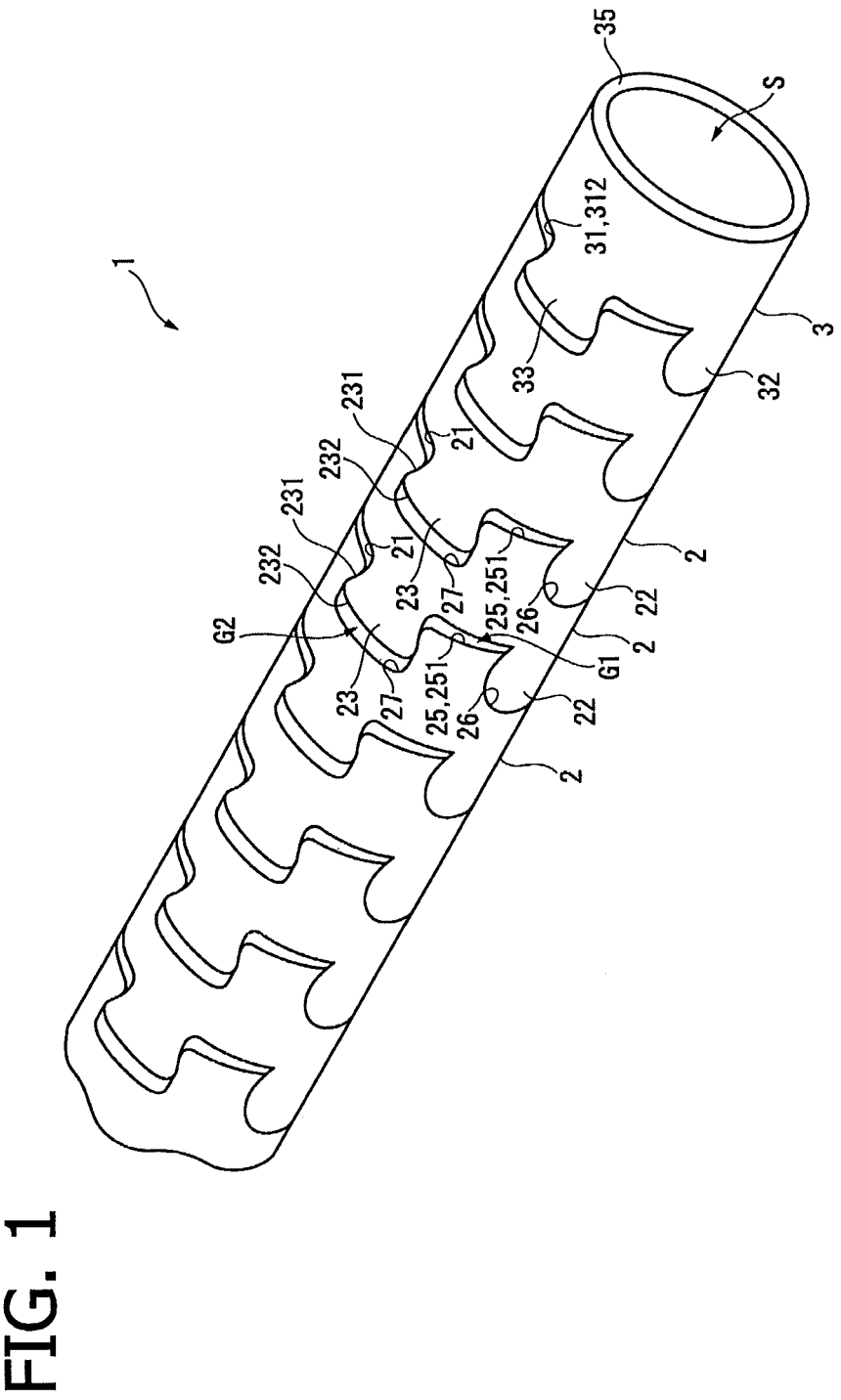
FIG. 1 is a perspective view of a flexible tube for medical instrument according to a first embodiment of the present invention.

In FIG. 1, a flexible tube for medical instrument (hereinafter referred to simply as the flexible tube) 1 is used for a medical instrument such as a catheter or an endoscope. The flexible tube 1 has a lumen S which is for an inserted body such as a guide wire to be inserted thereinto and passed therethrough.

The flexible tube 1 includes a plurality of tubular bodies 2 and a distal section 3. The tubular bodies 2 and the distal section 3 are connected together in a relatively turnable manner and along the axial direction of the flexible tube 1.

Figure 2:
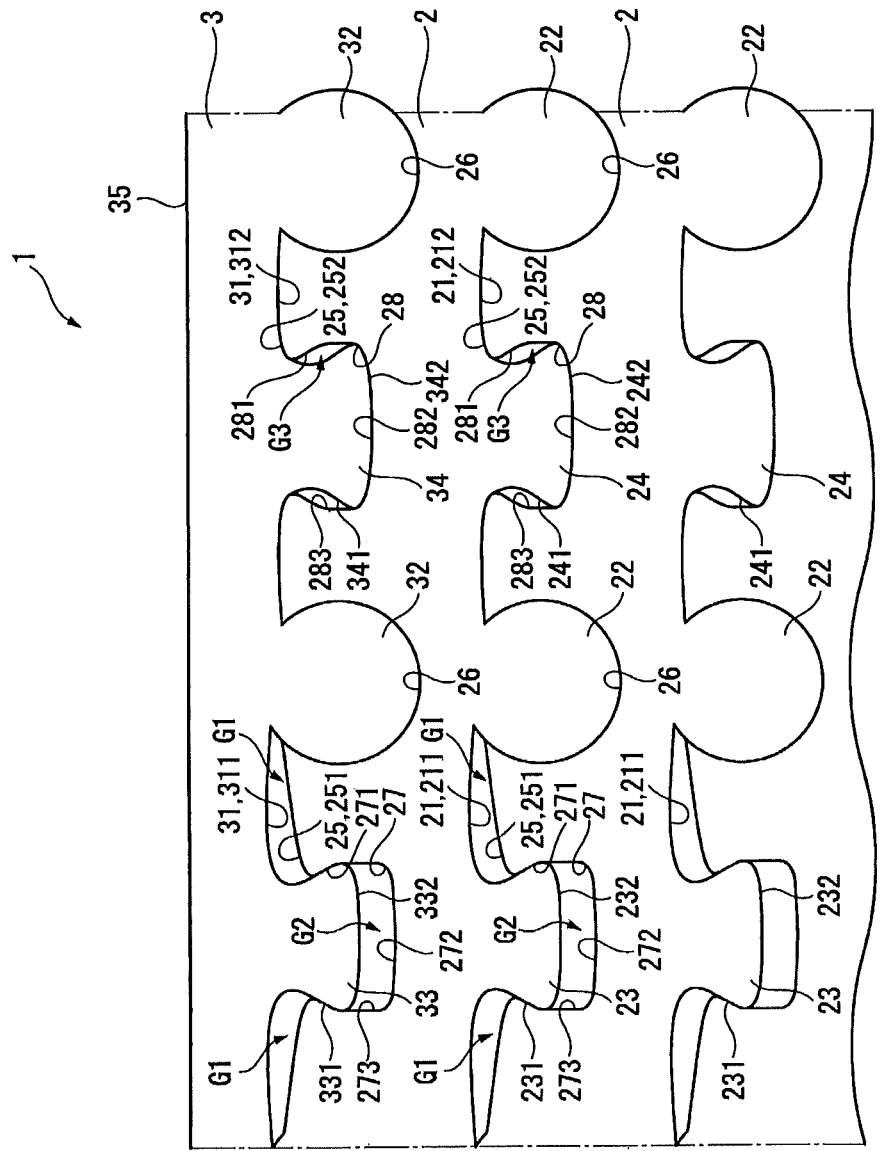
FIG. 2 is a development of the flexible tube for medical instrument of FIG. 1.

In FIG. 2, each tubular body 2 has pivotal sections 22, a first projection 23 as a projection, and a second projection 24 as a projection, which are provided at an end edge 21 on one side with respect to the connecting direction (the axial direction of the tubular body 2). The tubular body 2 also has turning support sections 26, a first recess 27 as a recess, and a second recess 28 as a recess, which are provided at an end edge 25 on the other side with respect to the connecting direction.

Figure 3:
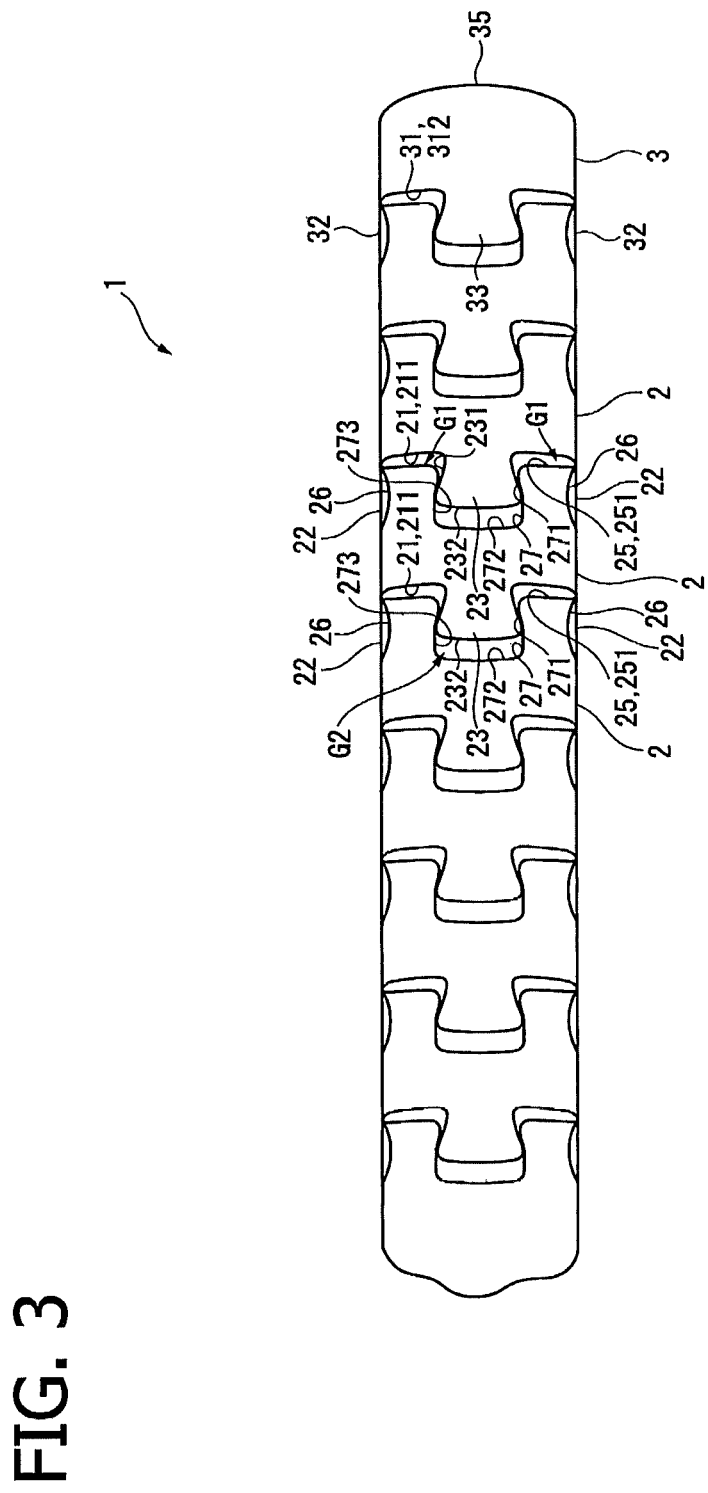
FIG. 3 is a plan view, as viewed from one side, of the flexible tube for medical instrument of FIG. 1.
Figure 4:
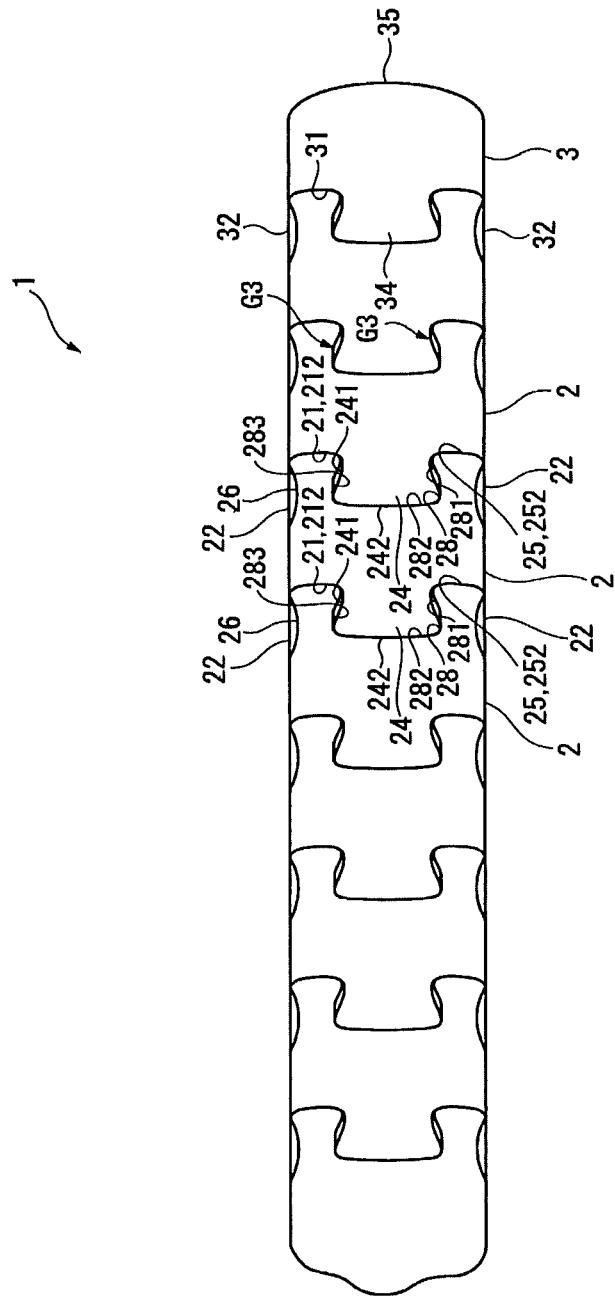
FIG. 4 is a plan view, as viewed from the other side, of the flexible tube for medical instrument of FIG. 1.

As shown in FIGS. 3 and 4 also, a pair of the pivotal sections 22 is provided at those positions of the end edge 21 which are symmetrical with each other about the center axis of the tubular body 2. The pivotal sections 22 are each projected in the axial direction of the tubular body 2 from the end edge 21, and formed in a circular shape in plan view.

The first and second projections 23 and 24 are provided on one side and the other side of the pivotal section 22 of the end edge 21, at positions different from the positions of the pivotal sections 22. Specifically, the first and second projections 23 and 24 are provided at those positions which are each located in the middle between the pivotal sections 22 and which are symmetrical with each other about the center axis of the tubular body 2. The projections 23 and 24 are each formed to project in the connecting direction of the tubular bodies 2 from the end edge 21, and the amount of projection of the first projection 23 is smaller than that of the second projection 24. In addition, the projections 23 and 24 respectively have enlarged-width parts 231 and 241 whose widths in the direction orthogonal to the projecting direction of the projections 23 and 24 are gradually enlarged along the projecting direction. Furthermore, tip edges 232 and 242 of the projections 23 and 24 are each curved to bulge along the projecting direction of the projections 23 and 24.

A pair of the turning support sections 26 of one tubular body 2 is provided at those positions of the end edge 25 which are symmetrical with each other about the center axis of the tubular body 2, and support the pivotal sections 22 of the tubular body 2 connected to the one tubular body 2. The turning support sections 26 are each formed by cutting out the end edge 25 in a circular shape. The turning support sections 26 and the pivotal sections 22 together constitute a hinge structure.

The first and second recesses 27 and 28 are provided on one side and the other side of the turning support section 26 of the end edge 25, at positions which are each located in the middle between the turning support sections 26 and which are symmetrical with each other about the center axis of the tubular body 2. The recesses 27 and 28 are each formed by cutting out the end edge 25 in a retracted and recessed shape. The amount of retraction of the first recess 27 from the end edge 25 is greater than that of the second recess 28. In addition, the recesses 27 and 28 respectively include reduced-width parts 271 and 281 whose widths in the direction orthogonal to the depth direction of the recesses 27 and 28 gradually decrease along the depth direction, and sliding contact parts 273 and 283 of which the widths in the direction orthogonal to the depth direction are constant along the depth direction and which respectively make sliding contact with the projections 23 and 24. Furthermore, bottom edges 272 and 282 of the recesses 27 and 28 are each curved to bulge along the depth direction of the recesses 27 and 28.

The distal section 3 is formed in a circular tube-like shape. An end edge 31 on one side, namely, an end edge 31 near the tubular body 2, of the distal section 3 is provided with pivotal sections 32, a first projection 33, and a second projection 34. The pivotal sections 32, the first projection 33, and the second projection 34 are formed in the same manner as the pivotal sections 22, the first projection 23, and the second projection 24 of the tubular body 2, respectively. On the other hand, an end edge 35 on the other side of the distal section 3 is provided with no turning support section, no first recess, and no second recess.

In the flexible tube 1 as above, each tubular body 2 and the distal section 3 are relatively turnably connected together through engagement of the pivotal sections 22 and 32 of the connected tubular body 2 and the distal section 3 with the turning support sections 26. In this case, the first projections 23 and 33 of the connected tubular body 2 and the distal section 3 are engaged with the first recesses 27 of the tubular bodies 2, and the second projections 24 and 34 of the connected tubular body 2 and the distal section 3 are engaged with the second recesses 28 of the tubular bodies 2. When the flexible tube 1 is curved, the maximum-width portions of the enlarged-width parts 231, 241, 331 and 341 of the projections 23, 24, 33 and 34 make sliding contact with the sliding contact parts 273 and 283 of the recesses 27 and 28. In other words, the projections 23, 24, 33 and 34 and the recesses 27 and 28 are constantly in contact with each other in the circumferential direction of the flexible tube 1, irrespectively of the curved degree of the flexible tube 1.

Here, of the connecting-directionally end edges 21 and 25 of each tubular body 2, a region 211 near the first projection 23 and a region 251 near the first recess 27 are so formed that the connecting-directional length of the tubular body 2 gradually decreases as the distance from the center of turning of the pivotal section 22 (which is the turning axis of the hinge structure) increases. In other words, a gap G1 is provided between the regions 211 and 311 near the first projections 23 and 33 of each end edges 21 and 31 and the region 251 near the first recess 27 of the end edge 25 facing the end edges 21 and 31 under consideration, respectively. Besides, the gap (spacing) is enlarged gradually as the distance from the pivotal section 22 or the turning support section 26 increases.

In addition, a gap G2 is provided respectively between tip edges 232 and 332 of the first projections 23 and 33 and a bottom edge 272 of the first recess 27 with which the first projections 23 and 33 are engaged.

In contrast, no gap is provided between regions 212 and 312 near the second projection 24 of the end edges 21 and 31 and a region 252 near the second recess 28 of the end edge 25, and no gap is provided between tip edges 242 and 342 of the second projections 24 and 34 and a bottom edge 282 of the second recess 28 with which the second projections 24 and 34 are engaged, respectively. On the other hand, a gap G3 axially extends between the enlarged-width parts 241 and 341 of the second projections 24 and 34 and the reduced-width part 281 of the second recess 28, respectively.

Figure 5:
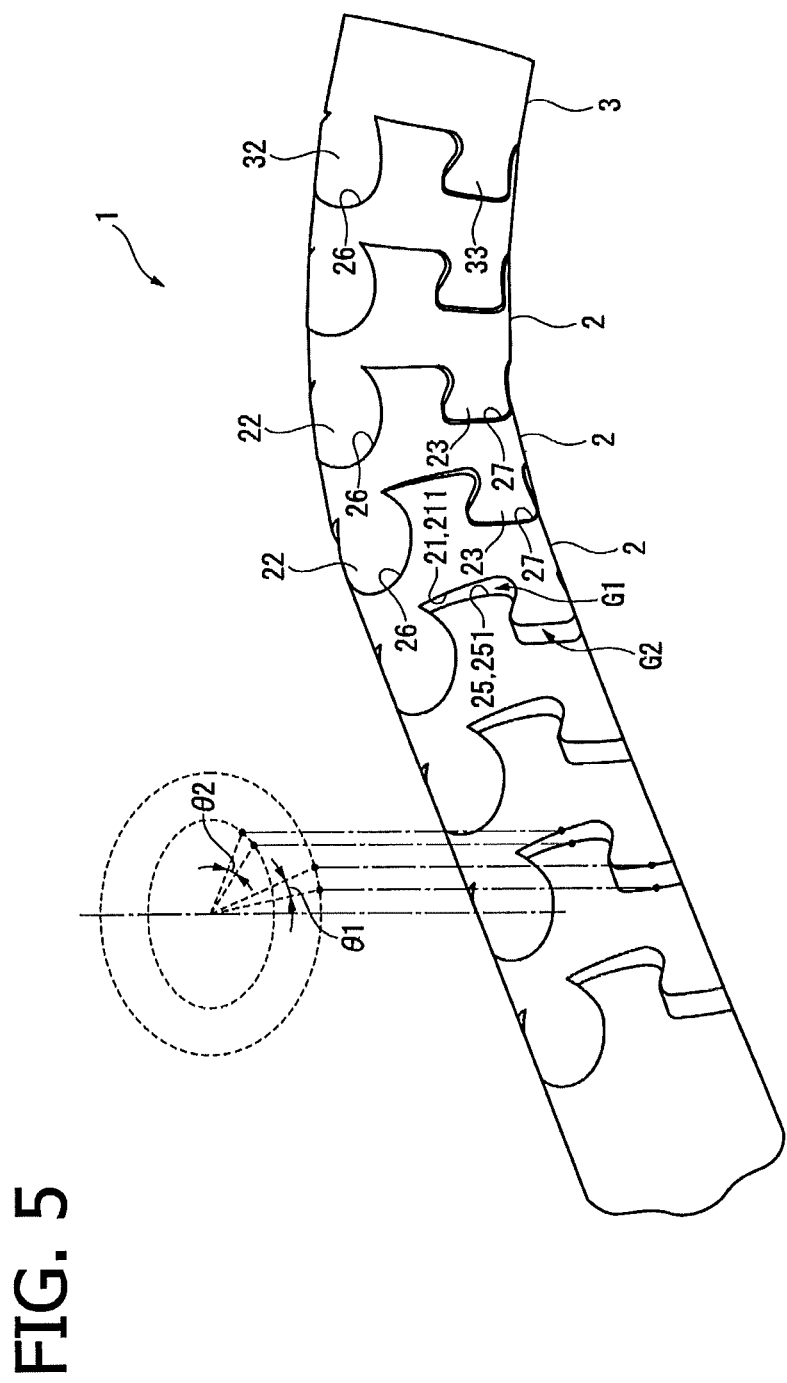
FIG. 5 is a perspective view, as viewed from one side, of a condition where the flexible tube for medical instrument of FIG. 1 is curved.
Figure 6:
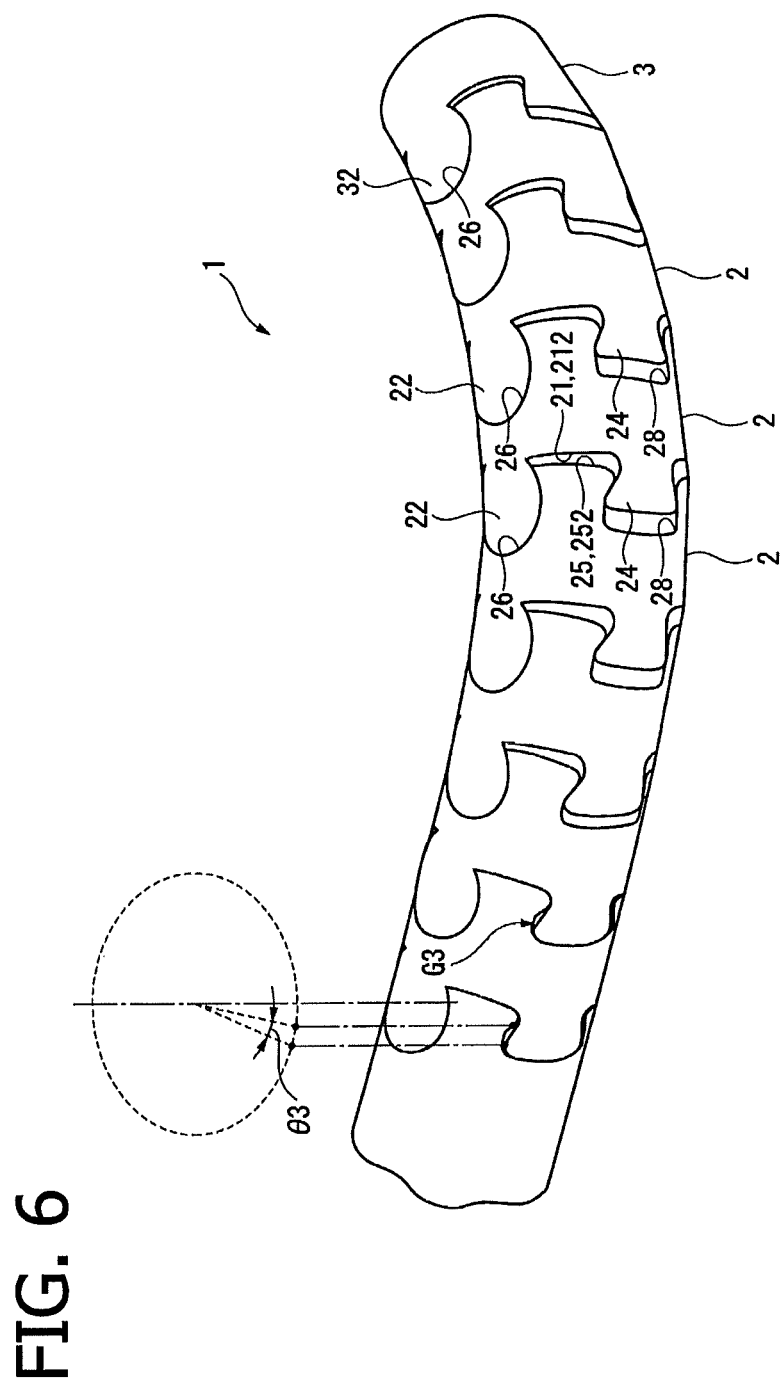
FIG. 6 is a perspective view, as viewed from the other side, of the condition where the flexible tube for medical instrument of FIG. 1 is curved.

Therefore, as shown in FIGS. 5 and 6, the tubular body 2 can be turned toward the first projections 23 and 33 and the first recess 27 by an amount corresponding to the gaps G1 to G3, centering around the pivotal sections 22 and 32; however, the tubular body 2 cannot be turned toward the second projections 24 and 34 and the second recess 28. Thus, the flexible tube 1 is so configured that it can be curved in only one direction.

Specifically, the regions 211, 251 and 311 of the end edges 21, 25 and 31, the tip edges 232 and 332, the bottom edges 272, the enlarged-width parts 241 and 341, and the reduced-width parts 281 are so formed that angles θ1, θ2 and θ3 formed by intersections with concentric circles with the pivotal sections 22 and 32 as a center of rotation are equal to one another. This ensures that when the flexible tube 1 is curved to a maximum extent, the regions 211 and 311 of the end edges 21 and 31 and the regions 251 of the end edges 25 can be put into contact, the tip edges 232 and 332 and the bottom edges 272 can be put into contact, and the enlarged-width parts 241 and 341 and the reduced-width parts 281 can be put into contact, with each other, simultaneously. In addition, the areas of contact in this instance can be enlarged. Accordingly, the rigidity in the axial direction of the flexible tube 1 when the flexible tube 1 is curved to the maximum can be enhanced greatly.

On the other hand, the regions 212 and 312 of the end edges 21 and 31 and the regions 252 of the end edges 25 are put into contact, and the tip edges 242 and 342 and the bottom edges 282 are put into contact, with each other, when the flexible tube 1 is in a straight state. Accordingly, the rigidity in the axial direction of the flexible tube 1 when the flexible tube 1 is in the straight state can be significantly enhanced.

Besides, in order to enable the flexible tube 1 to be introduced into a living body, the outside diameter of the flexible tube 1 must be set as small as about several millimeters. On the other hand, since an inserted body such as a guide wire is inserted into and passed through the inside of the flexible tube 1, it is desirable to set the inside diameter of the flexible tube 1 to be as large as possible. Therefore, the flexible tube 1 is made to have an outside diameter of about 1 to 20 mm (preferably, 1 to 5 mm), an inside diameter of about 0.4 to 18 mm (preferably, 0.4 to 4.4 mm), and a material thickness of about 0.1 to 1 mm (preferably 0.25 to 0.5 mm).

Such a flexible tube 1 can be obtained, for example, by putting a stainless steel-made circular tubular member with the above-mentioned outside diameter and inside diameter to laser beam machining. Where laser beam machining is employed, it is possible, by simply cutting the circular tubular member with a laser beam, to easily obtain the flexible tube 1 in a state where the tubular bodies 2 and the distal section 3 are connected to one another.

It is to be noted that the material for the flexible tube 1 and the production method are not limited to the above examples but can be selected arbitrarily.

According to this embodiment, the following effects can be obtained.

Since the recesses 27 and 28 of the tubular body 2 are engaged with the projections 23, 24, 33 and 34 of the connected tubular body 2 or the distal section 3, external forces applied to the flexible tube 1 can be received by the recesses 27 and 28 and the projections 23, 24, 33 and 34. This ensures that the external forces can be received also by other sections than the pivotal sections 22 and 32 and the turning support sections 26, so that sufficient rigidity against external forces can be secured.

In addition, since the projections 23, 24, 33 and 34 are engaged with the recesses 27 and 28 of the connected tubular body 2, the tubular bodies 2 are, or the tubular body 2 and the distal section 3 are, bridged to each other by the projections 23, 24, 33 and 34. As a result, a body inserted into the flexible tube 1 is guided through contact with the projections 23, 24, 33 and 34, so that the inserted body is not liable to be caught by the connecting-directionally end edges 21, 25 and 31 of the tubular bodies 2. Consequently, the inserted body can be easily inserted into and passed through the flexible tube 1.

Furthermore, as the flexible tube 1 is curved, the spacing between the second recess 28 located on the outer side with respect to the curvature and the second projection 24 or 34 engaged with the second recess 28 is enlarged, whereby the projection 24 or 34 would be moved in a direction for disengagement from the second recess 28. In this case, however, the enlarged-width part 241 or 341 of the second projection 24 or 34 is fitted into the reduced-width part 281 of the second recess 28 in a wedge-like manner, so that the second projection 24 or 34 is caught on the second recess 28. Accordingly, tensile rigidity of the flexible tube 1 when the flexible tube 1 is curved to the maximum can be enhanced, and rigidity of the flexible tube 1 can be more enhanced. Further, if the first recesses 27 and the first projections 23 and 33 located on the inner side with respect to the curvature are preliminarily engaged with each other when the enlarged-width parts 231 and 331 of the first projections 23 and 33 are fitted in the reduced-width parts 271 of the first recesses 27 in a wedge-like manner, in a straight state of the flexible tube 1, then the tensile rigidity of the flexible tube 1 in the straight state can also be enhanced.

In addition, the recesses 27 and 28 are provided with the sliding contact parts 273 and 283 (with which the projections 23, 24, 33 and 34 make sliding contact) in the depth direction. This ensures that the recesses 27 and 28 and the projections 23, 24, 33 and 34 continue to make contact with each other in their width direction, namely, in the circumferential direction of the tubular bodies 2 and the distal section 3, irrespectively of the curved degree of the flexible tube 1. Therefore, when a rotating force about the axis of the tubular bodies 2 is exerted on the flexible tube 1, the rotating force can be received also by other sections than the pivotal sections. As a result, torsional rigidity of the flexible tube 1 can be enhanced, and rigidity of the flexible tube can be more enhanced.

Furthermore, the maximum-width portions of the enlarged-width parts 231, 241, 331 and 341 make sliding contact with the sliding contact parts 273 and 283 of the recesses 27 and 28. This eliminates the need to provide other parts for sliding contact with the recesses 27 and 28 than the enlarged-width parts 231, 241, 331 and 341. Therefore, the sliding contact state between the projections 23, 24, 33 and 34 and the recesses 27 and 28 can be maintained, while suppressing the amount of projection of the projections 23, 24, 33 and 34 as well as the depth of the recesses 27 and 28. As a result, rigidity of the projections 23, 24, 33 and 34 and the recesses 27 and 28 can be enhanced, and the length of the tubular bodies 2 to be connected together can be shortened. Accordingly, rigidity of the flexible tube 1 can be further enhanced, and the length of the curved portion of the flexible tube 1 can be reduced.

In addition, tip edges 232, 242, 332 and 342 of the projections 23, 24, 33 and 34 and the bottom edges 272 and 282 of the recesses 27 and 28 are each formed in a curved line shape. Therefore, a body inserted into the flexible tube 1 can be guided along the shapes of the tip edges 232, 242, 332 and 342 or the bottom edges 272 and 282. This makes it possible to restrain the inserted body from being caught on the tip edges 232, 242, 332 and 342 or the bottom edges 272 and 282. Accordingly, the inserted body can be speedily inserted into and passed through the flexible tube 1.

Besides, the end edges 21 and 25 with respect to the connecting direction of the tubular bodies 2 are each so formed that the length of the tubular bodies 2 in the connecting direction of the tubular bodies 2 gradually decreases as the distance from the turning axis increases. Therefore, the spacing between the opposed end edges 21 and 25 of the tubular bodies 2 connected together and the spacing between the end edge 25 of the tubular body 2 and the end edge 31 of the distal section 3 are enlarged as the distance from the turning axis increases. This ensures that even where the spacing between the end edges 21, 25 and 31 is reduced by turning of the tubular bodies 2 when the flexible tube 1 is curved, it is possible to prevent the end edges 21, 25 and 31 from interfering with each other.

Second Embodiment

Now, a second embodiment of the present invention will be described below, based on FIGS. 7 and 8.

A flexible tube 1 in this embodiment differs from the flexible tube in the first embodiment in that it has first and second tubular bodies 2A and 2B as tubular bodies differing in shape, and the first and second tubular bodies 2A and 2B are alternately connected together.

Figure 7:
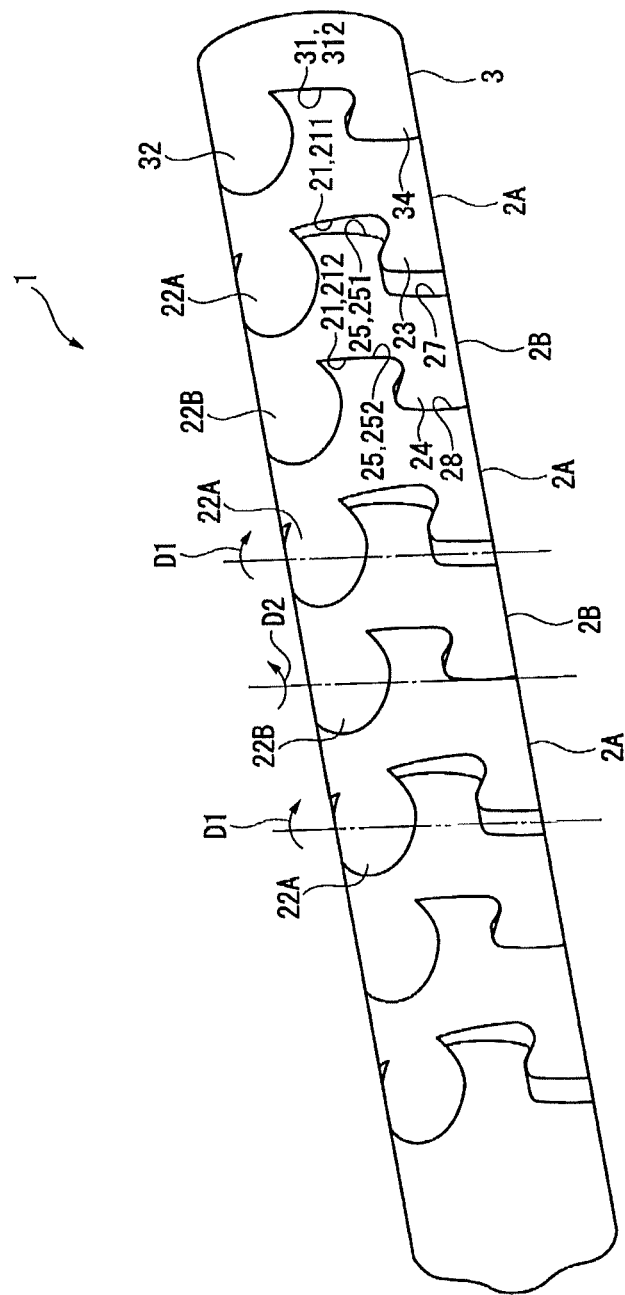
FIG. 7 is a perspective view of a flexible tube for medical instrument according to a second embodiment of the present invention.
Figure 8:
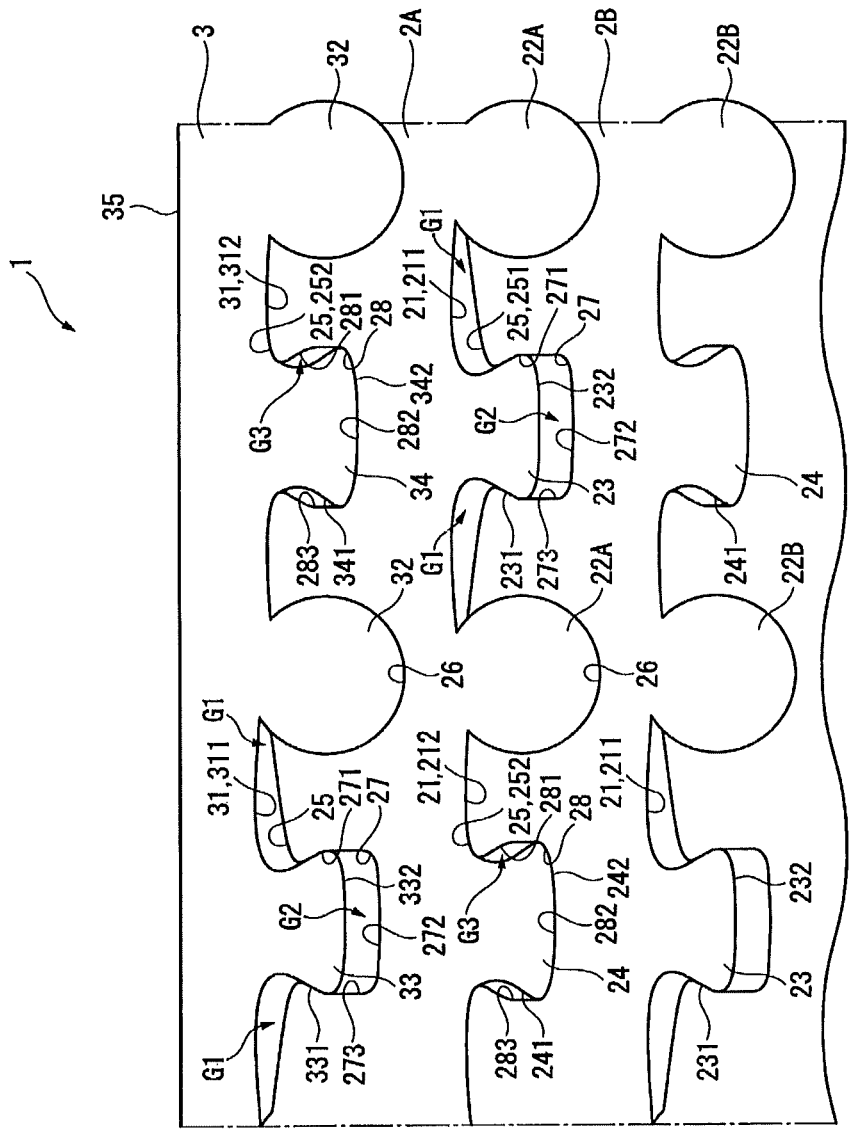
FIG. 8 is a development of the flexible tube for medical instrument of FIG. 7.

Specifically, as shown in FIGS. 7 and 8, the first tubular body 2A has a configuration in which the positions of the first projection 23 and the second projection 24 are reversed, in relation to the tubular body 2 in the first embodiment.

On the other hand, the second tubular body 2B has a configuration in which the positions of the first recess 27 and the second recess 28 are reversed, in relation to the tubular body 2 in the first embodiment.

In this case, the first tubular body 2A and the second tubular body 2B are permitted to undergo relative rotation in one direction indicated by arrow D1 in FIG. 7, centering around the pivotal sections 22A of the first tubular body 2A. Further, the tubular bodies 2A and 2B are permitted to undergo relative rotation in the other direction indicated by arrow D2 in FIG. 7, centering around the pivotal sections 22B of the second tubular body 2B. In other words, the flexible tube 1 can be curved in two opposite directions.

According to this embodiment, the following effects can be obtained, in addition to the effects of the first embodiment.

Since the flexible tube 1 is so configured that it can be curved in two opposite directions, the degree of freedom in curvature of the flexible tube 1 can be enhanced. For instance, the flexible tube 1 can be curved toward the viewer's side of FIG. 7, and can be curved toward the opposite side. In addition, by curving the flexible tube 1 partly toward the viewer's side of FIG. 7 and partly toward the opposite side, it is possible to curve the flexible tube 1 into an S-shaped form. Accordingly, utility of the flexible tube 1 can be more enhanced.

Third Embodiment

Figure 9:
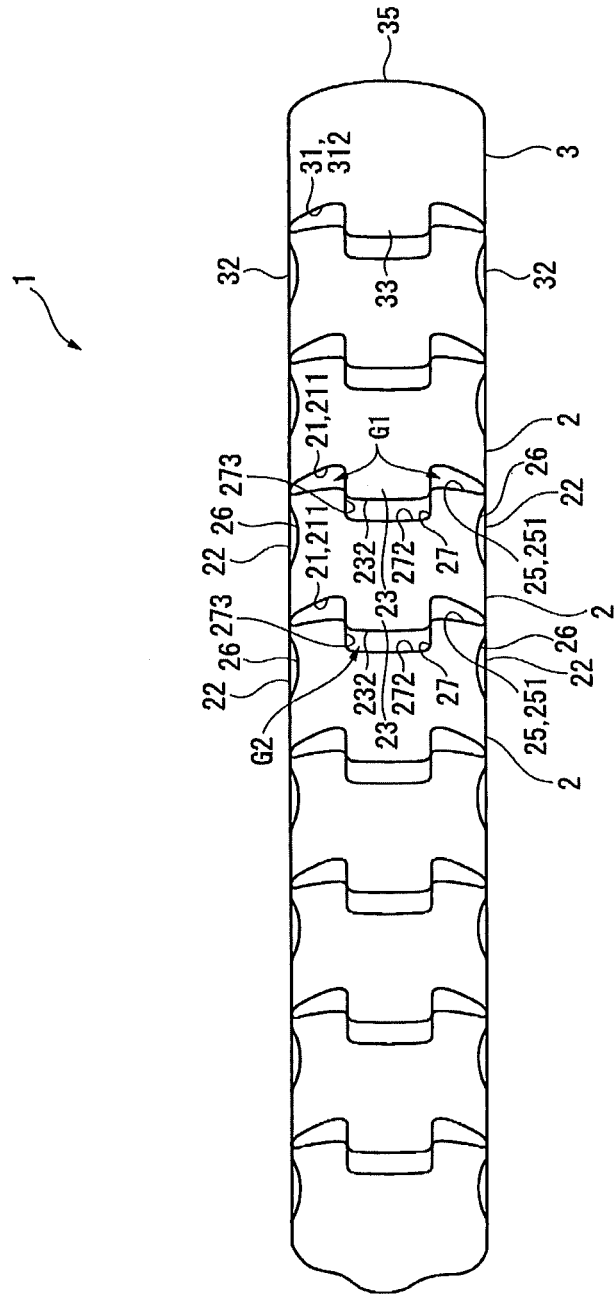
FIG. 9 is a plan view of a flexible tube for medical instrument according to a third embodiment of the present invention.
Figure 10:
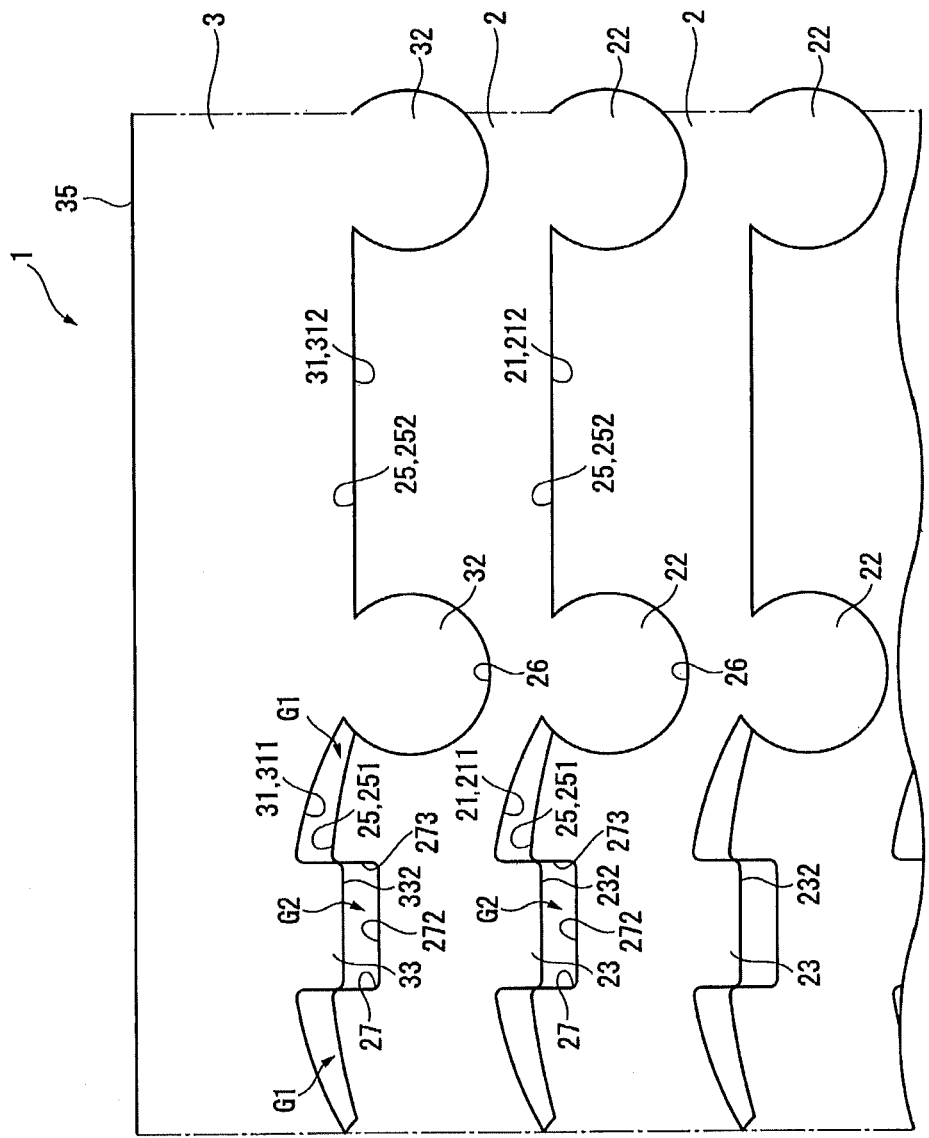
FIG. 10 is a development of the flexible tube for medical instrument of FIG. 9.

Now, a third embodiment of the present invention will be described below, based on FIGS. 9 and 10.

A flexible tube 1 in this embodiment differs from the flexible tube in the first embodiment in the shapes of the first projection 23 and the first recess 27 and in the shapes of those regions of the end edges 21, 25 and 31 which are on the opposite side from the first projections 23 and 33 or the first recess 27.

Specifically, the first projection 23 is formed in a rectangular shape in plan view, and the first recess 27 is also formed in a rectangular shape in plan view, correspondingly to the first projection 23. On the other hand, those regions of the end edges 21 and 31 which are on the opposite side from the first projections 23 and 33 and that region of the end edge 25 which is on the opposite side from the first recess 27 are formed to be straight in side view. In other words, each of the tubular bodies 2 and the distal section 3 is provided with no second projection 24 or 34 and no second recess 28.

Besides, when the flexible tube 1 is in a straight state, a gap G2 is provided between the tip edge 232 of the first projection 23 and the bottom edge 272 of the first recess 27, and between the region near the first projection 23 of the end edge 21 and the region near the first recess 27 of the end edge 25. On the other hand, no gap is provided between each of those regions of the end edges 21 and 31 which are on the opposite side from the first projections 23 and 33 and that region of the end edge 25 which is on the opposite side from the first recess 27. Therefore, the flexible tube 1 can be curved only toward the first projection 23 and the first recess 27, centering around the pivotal sections 22 and the turning support sections 26.

According to this embodiment, the following effect can be obtained.

Since the tubular bodies 2 and the distal section 3 are formed in simple shapes, it is easy to form the tubular bodies 2 and the distal section 3. Accordingly, the flexible tube 1 can be manufactured easily, with a reduction in manufacturing cost.

APPLICATION EXAMPLES OF ABOVE-DESCRIBED EMBODIMENTS

Now, examples of application of the flexible tubes according to the above-described embodiments to medical instruments will be described below, based on the drawings.

First Application Example

Figure 11:
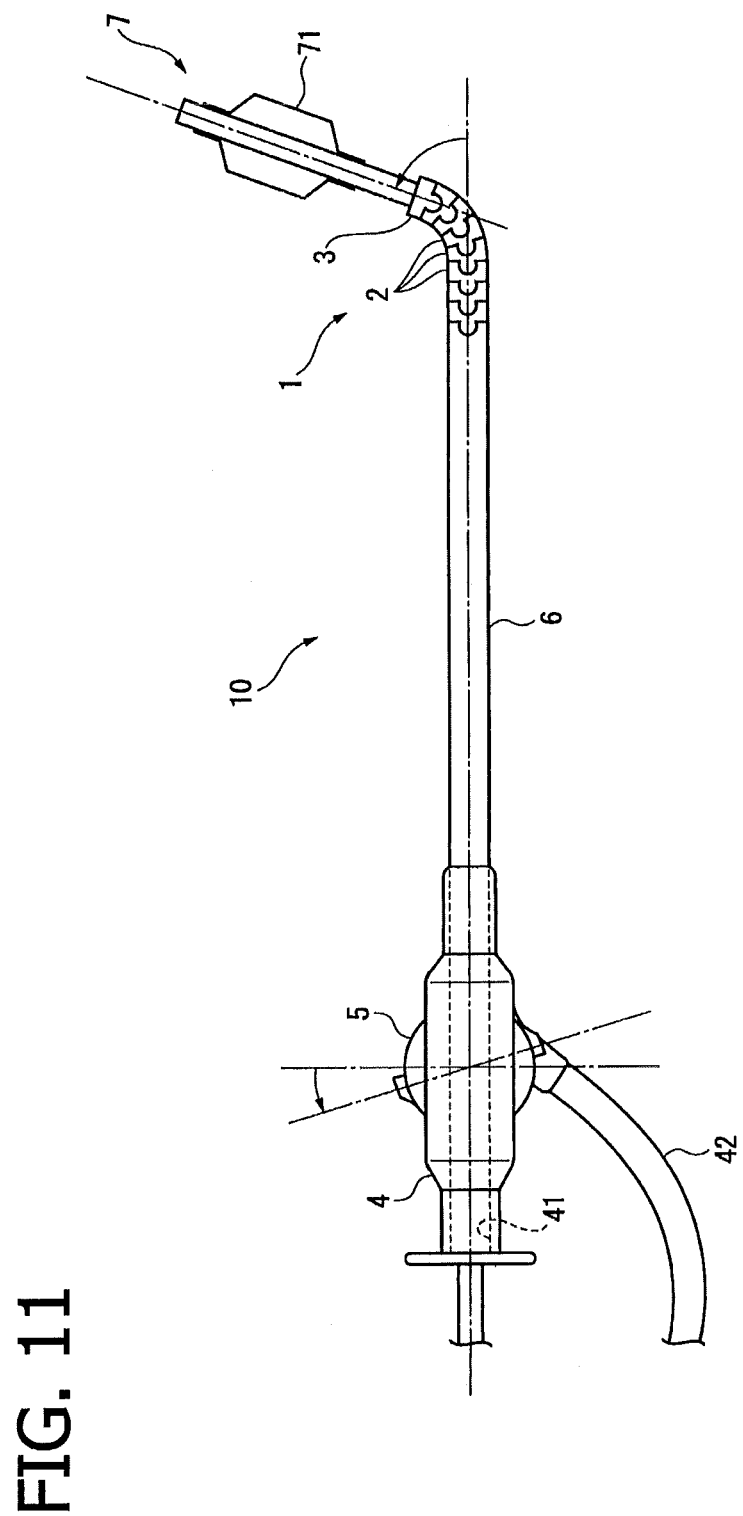
FIG. 11 is a plan view of a medical instrument to which the flexible tube for medical instrument according to the above embodiment has been applied.

A medical instrument 10 according to this application example, as shown in FIG. 11, includes a guiding catheter 6, and a balloon catheter 7 which has a balloon 71 as an expansion body and which is disposed inside the guiding catheter 6 so that it can be advanced and retracted. The guiding catheter 6 includes a flexible tube 1 according to any of the first to third embodiments described above, a hub 4 connected to a proximal portion of the flexible tube 1, and position fixing means 5 for fixing the curved position of the flexible tube 1.

The hub 4 has an introduction passage 41 through which the lumen S of the flexible tube 1 and the exterior communicate with each other. An inserted body such as the balloon catheter 7 can be inserted into the lumen S of the flexible tube 1 through the introduction passage 41. In addition, the flexible tube 1 is provided with a discharge passage 42 branched from the introduction passage 41 so that a body fluid can be discharged through the discharge passage 42.

The position fixing means 5 is turnably provided on the hub 4, and the position fixing means 5 and a distal section 3 of the flexible tube 1 are interconnected by a wire or the like (not shown). Therefore, by rotating the position fixing means 5, it is possible to control a curved position of the flexible tube 1, and to fix the curved position.

The medical instrument 10 configured as above can be used, for example, for treatment of sinusitis. Specifically, the guiding catheter 6 is inserted via the nose, and, while curving the flexible tube 1 in conformity with the internal shape of the nasal cavity, it is delivered to a paranasal sinus. In this condition, the balloon catheter 7 is inserted into and passed through the lumen S of the guiding catheter 6, and the balloon 71 is inflated in a somewhat occluded natural ostium at the paranasal sinus, thereby dilating the natural ostium.

The paranasal sinuses are present at four positions, and their positions greatly vary from person to person. In addition, the passage for reaching a paranasal sinus is narrow. Conventionally, therefore, a plurality of guiding catheters differing in curvature shape have been used according to the internal shape of the nasal cavity, the position of the target paranasal sinus, etc.

According to this example, on the other hand, the medical instrument 10 has the flexible tube 1 which can be curved, so that the guiding catheter 6 can be easily delivered to the paranasal sinus while varying the curved degree of the flexible tube 1. This eliminates the need for replacement of the guiding catheter 6. Consequently, it is possible to reduce the number of medical instruments required for treatment of sinusitis, and to reduce the labor and time required for replacement of the guiding catheter 6.

In addition, since the medical instrument 10 has the above-mentioned flexible tube 1, the guiding catheter 6 can be inserted into a living body in a freely curvable manner while securing rigidity against external forces. Besides, with the balloon catheter 7 expanded in a stenosed part of a paranasal sinus, it is possible to dilate and treat the stenosed part.

Second Application Example

Figure 12:
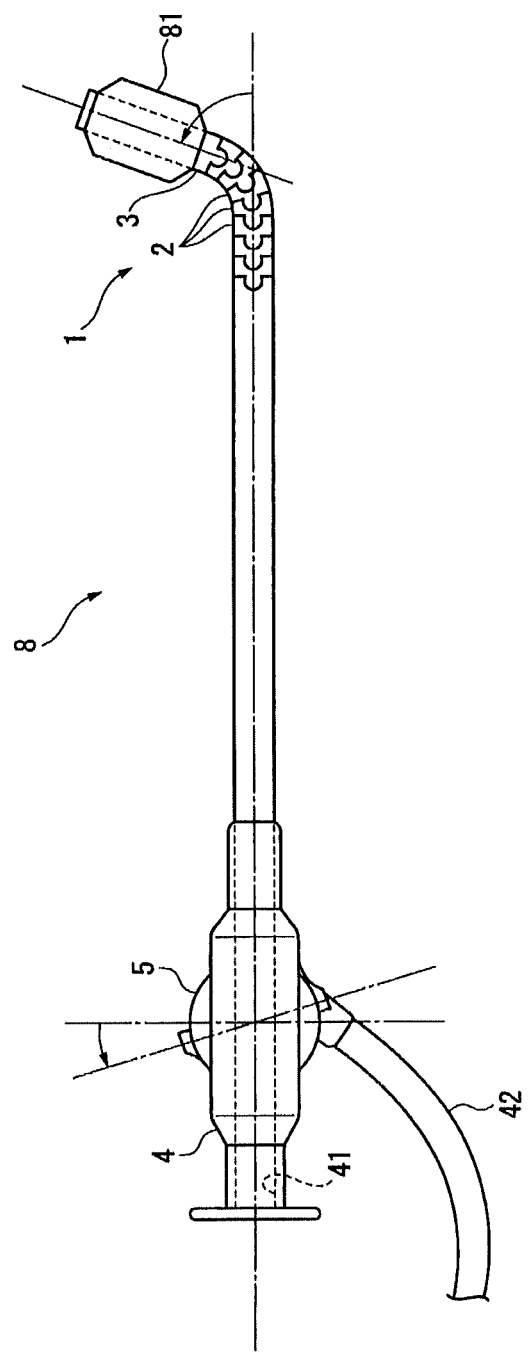
FIG. 12 is a plan view of another medical instrument to which the flexible tube for medical instrument according to the above embodiment has been applied.

A balloon catheter 8 as a medical instrument according to this application example, as shown in FIG. 12, includes a flexible tube 1 according to any of the first to third embodiments above, a hub 4 connected to a proximal portion of the flexible tube 1, position fixing means 5 for fixing the curved position of the flexible tube 1, and a balloon 81 as an expansion body provided at a distal portion of the flexible tube 1.

With the balloon catheter 8 configured as above, also, the same effects as those of the first application example can be obtained.

Incidentally, the present invention is not restricted to the above-described embodiments, and modifications and improvements and the like within the scope in which the object of the invention can be attained are embraced in the invention.

For instance, the projections 23 and 24 of the tubular body 2 have been provided at the end edge 21 provided with the pivotal sections 22, and the recesses 27 and 28 have been provided at the end edge 25 provided with the turning support sections 26, in the above embodiments. This configuration, however, is not restrictive. For example, the projections 23 and 24 may be provided at the end edge 25, and the recesses 27 and 28 may be provided at the end edge 21.

In the first and second embodiments, the projections 23 and 24 have been provided with the enlarged-width parts 231 and 241 and the recesses 27 and 28 have been provided with the reduced-width parts 271 and 281. However, the projections 23 and 24 and the recesses 27 and 28 may be formed in a rectangular shape in plan view, like in the third embodiment. In this case, the amount of engagement of the projections 23 and 24 with the recesses 27 and 28 in the axial direction may be set greater than the amount of relative movement of the recesses 27 and 28 and the projections 23 and 24 at the time of maximum turning. Such a setting ensures that the projections 23 and 24 and the recesses 27 and 28 can be engaged with each other, irrespectively of the state of turning. Therefore, the projections 23 and 24 and the recesses 27 and 28 can be prevented from disengagement, even when the flexible tube 1 is curved to maximum, and rigidity of the flexible tube 1 can be sufficiently maintained.

While the flexible tube 1 has been applied to a guiding catheter 6 in the application examples of the embodiments, this is not restrictive of the medical instrument according to the present invention. In short, the medical instrument according to the present invention may be any medical instrument as long as it has a flexible tube in which a plurality of tubular bodies are connected together. For instance, the flexible tube 1 may be applied to other kinds of catheters than the guiding catheter 6, and also to endoscopes. In addition, the cross-sectional shape of the tubular bodies is not restricted to a true circle but may be an ellipse or a polygon, for example; thus, the tubular body may be any tubular member which has point symmetry in a plane orthogonal to the axial direction thereof.

The present invention is applicable to any medical instrument provided with a flexible tube.

What is claimed is:

1. A flexible tube for medical instrument, comprising
a plurality of tubular bodies, one of the plurality of tubular bodies relatively turnably connected to an adjacent one of the plurality of tubular bodies by a hinge structure, wherein
each of the tubular bodies includes
a pivotal section which is provided at a first end edge in a connecting direction of the plurality of tubular bodies and forms the hinge structure,
a turning support section which is provided at a second end edge in the connecting direction of the plurality of tubular bodies and supports the pivotal section of the one of the plurality of tubular bodies connected to the adjacent one of the plurality of tubular bodies,
a projection which is provided at either one of the first end edge and the second end edge, and which is projected in the connecting direction from a position different from the position of the pivotal section or the turning support section, and
a recess which is provided at the other of the first end edge and the second end edge, and which is engaged with the projection of the one of the plurality of tubular bodies connected to the adjacent one of the plurality of tubular bodies, and
wherein
the projection has an enlarged-width part whose width in a direction orthogonal to a projecting direction away from the first end edge of the tubular body gradually increases along the projecting direction,
the recess has a reduced-width part whose width in a direction orthogonal to a depth direction toward a bottom edge of the recess gradually decreases along the depth direction, the recess has a sliding contact part which is so formed that its width in a direction orthogonal to the depth direction of the recess is constant along the depth direction and with which the projection makes sliding contact, and a maximum-width portion of the enlarged-width part makes sliding contact with the sliding contact part.

2. The flexible tube for medical instrument according to claim 1, wherein a tip edge of the projection makes contact with the bottom edge of the recess.

3. The flexible tube for medical instrument according to claim 1, wherein the projection and the recess are provided on either of one side and the other side of a turning axis of the hinge structure, the tip edge of the projection on the one side makes contact with the bottom edge of the recess on the one side when the flexible tube is in a straight state, and the tip edge of the projection on the other side makes contact with the bottom edge of the recess on the other side when the flexible tube is bent.

4. The flexible tube for medical instrument according to claim 1, wherein a tip edge of the projection is curved to bulge in a projecting direction of the projection, and the bottom edge of the recess is curved to bulge in a depth direction of the recess.

5. The flexible tube for medical instrument according to claim 1, wherein the first and second end edges of each tubular body are so formed that the width of the tubular body in the connecting direction gradually decreases as the distance from the turning axis of the hinge structure increases.

6. A medical instrument comprising:

a flexible tube for medical instrument, including a plurality of tubular bodies, one of the plurality of tubular bodies relatively turnably connected to an adjacent one of the plurality of tubular bodies by a hinge structure, wherein each of the tubular bodies includes a pivotal section which is provided at a first end edge in a connecting direction of the plurality of tubular bodies and forms the hinge structure, a turning support section which is provided at a second end edge in the connecting direction of the plurality of tubular bodies and supports the pivotal section of the one of the plurality of tubular bodies connected to the adjacent one of the plurality of tubular bodies, a projection which is provided at either one of the first end edge and the second end edge, and which is projected in the connecting direction from a position different from the position of the pivotal section or the turning support section, and a recess which is provided at the other of the first end edge and the second end edge, and which is engaged with the projection of the one of the plurality of tubular bodies connected to the adjacent one of the plurality of tubular bodies; and position fixing unit that is adapted to fix a curved position of the flexible tube, and wherein the projection has an enlarged-width part whose width in a direction orthogonal to a projecting direction away from the first end edge of the tubular body gradually increases along the projecting direction, the recess has a reduced-width part whose width in a direction orthogonal to a depth direction toward a bottom edge of the recess gradually decreases along the depth direction, and the recess has a sliding contact part which is so formed that its width in a direction orthogonal to the depth direction of the recess is constant along the depth direction and with which the projection makes sliding contact, and a maximum-width portion of the enlarged-width part makes sliding contact with the sliding contact part.

7. The medical instrument according to claim 6, comprising an expansion body which is provided on an outer circumference of the flexible tube or is provided in the flexible tube so as to be capable of being advanced and retracted and which is expanded in a radial direction of the flexible tube.

* * * * *